United States Patent
Landy, III et al.

(10) Patent No.: US 11,123,484 B2
(45) Date of Patent: Sep. 21, 2021

(54) PRESSURE RESPONSIVE FLUID FLOW CONTROL VALVES

(75) Inventors: John Joseph Landy, III, Billerica, MA (US); Michael Gildersleeve, Northborough, MA (US)

(73) Assignee: Belmont Instrument, LLC, Billerica, MA (US)

( * ) Notice: Subject to any disclaimer, the term of this patent is extended or adjusted under 35 U.S.C. 154(b) by 259 days.

(21) Appl. No.: 12/228,618

(22) Filed: Aug. 14, 2008

(65) Prior Publication Data
US 2009/0192446 A1 Jul. 30, 2009

Related U.S. Application Data

(62) Division of application No. 11/218,896, filed on Sep. 2, 2005, now abandoned.

(51) Int. Cl.
*A61M 5/168* (2006.01)
*G05D 16/06* (2006.01)

(52) U.S. Cl.
CPC ..... *A61M 5/16881* (2013.01); *G05D 16/0647* (2013.01); *Y10T 137/0379* (2015.04); *Y10T 137/7825* (2015.04); *Y10T 137/7836* (2015.04)

(58) Field of Classification Search
CPC ......... Y10T 137/7826; Y10T 137/7827; Y10T 137/7836; Y10T 137/0739; Y10T 137/7825; G05D 7/012; G05D 16/0647; A61M 5/16881
USPC ...... 137/12, 505.14, 505.41, 505.42, 505.43; 604/65, 99.04
See application file for complete search history.

(56) References Cited

U.S. PATENT DOCUMENTS

| | | | |
|---|---|---|---|
| 3,552,431 A * | 1/1971 | Schmidlin | 137/505.42 |
| 3,603,214 A * | 9/1971 | Murrell | 92/133 |
| 3,650,699 A * | 3/1972 | Beer | 422/510 |
| 4,146,055 A | 3/1979 | Ryder et al. | |
| 4,230,300 A | 10/1980 | Wiltse | |
| 4,256,104 A | 3/1981 | Muetterties et al. | |
| 4,316,460 A | 2/1982 | Genese et al. | |

(Continued)

*Primary Examiner* — William M McCalister
(74) *Attorney, Agent, or Firm* — Choate, Hall & Stewart LLP; William R. Haulbrook

(57) ABSTRACT

In one set of embodiments a selected section of tubular stock has its ends welded together to form a pillow-like pressure sensing device with an entry tube and an exit tube each configured to facilitate insertion of the pressure sensing device into the flow path of IV infusate in an IV administration set or system. Fluid pressure in excess of a predetermined amount reconfigures the pressure sensing device from a generally oval configuration to a generally circular configuration to restrict and/or cut off fluid flow into the device while permitting fluid flow from the device to reduce the fluid pressure again reconfiguring the device back to its generally oval configuration and permitting fluid flow into and through the device.

In other embodiments a fluid pressure sensing device is formed with a fluid entry chamber and a fluid exit chamber interconnected by a passageway and provided with a piston that reacts to an increase in fluid pressure above a predetermined amount to close off the interconnection between the chambers and fluid flow into the exit chamber. Continued fluid flow from the eit chamber results in a reduction of fluid therein and reopening of the fluid passageway between the chambers.

6 Claims, 4 Drawing Sheets

(56) References Cited

U.S. PATENT DOCUMENTS

| | | | |
|---|---|---|---|
| 4,332,369 A | | 6/1982 | Gordon et al. |
| 4,417,577 A | | 11/1983 | Genese et al. |
| 4,515,588 A | | 5/1985 | Amendolia |
| 4,537,387 A | * | 8/1985 | Danby et al. ................. 251/331 |
| 4,787,413 A | | 11/1988 | Baggers |
| 5,453,097 A | | 9/1995 | Paradis |
| 5,988,211 A | | 11/1999 | Cornell |
| 6,273,117 B1 | * | 8/2001 | McPhee ......................... 137/12 |
| 6,480,257 B2 | | 11/2002 | Cassidy et al. |
| 6,619,308 B2 | * | 9/2003 | Massengale et al. ........... 137/12 |
| 6,863,083 B2 | * | 3/2005 | Danby ...................... A45F 3/18 |
| | | | 137/384 |
| 6,892,755 B2 | * | 5/2005 | Black .................... A61M 5/152 |
| | | | 137/505.41 |
| 7,842,002 B2 | | 11/2010 | Mantle |
| 8,100,881 B2 | | 1/2012 | Hoffa |
| 8,439,960 B2 | | 5/2013 | Burnett et al. |
| 8,480,648 B2 | | 7/2013 | Burnett et al. |
| 8,672,884 B2 | | 3/2014 | Burnett et al. |
| 2003/0159734 A1 | * | 8/2003 | Danby ...................... A45F 3/18 |
| | | | 137/510 |
| 2007/0051409 A1 | * | 3/2007 | Landy et al. ................. 137/510 |

* cited by examiner

PRESSURE RESPONSIVE FLUID FLOW CONTROL VALVES

This application is a Division of applicants earlier filed patent application Ser. No. 11/218,896 filed on Sep. 2, 2005 now abandoned and assigned to the assignee of this application.

BACKGROUND OF THE INVENTION—FIELD OF THE APPLICATION

This invention relates to fluid-flow control valves, and more particularly to pressure responsive fluid-flow control valves particularly adapted for use with Intravenous (IV) infusion applications.

BACKGROUND OF THE INVENTION—DESCRIPTION OF PRIOR ART

In the administration of blood, and other fluids, it is sometimes required to rapidly increase the flow rate through the IV set to administer a large or larger volume of IV fluid. This is usually done by applying pressure to the IV line. One very common means of doing this is by manually squeezing a bladder or bulb in the IV administration set. When that is done, especially if the needle or cannula, or the other venous access device, cannot accommodate the sudden increase in fluid-flow, the pressure in the line usually quickly rises to a large and often dangerous value. Such pressure can easily exceed 20 psi (greater than 1,000 mm Hg) for a brief period. The use of a syringe to rapidly infuse fluid in pediatric patients through a small needle can produce a similar unacceptable pressure. The generally accepted safe pressure threshold is about 300 mm Hg, or about 6 psi. If the venous access device is not seated properly, this high pressure can be applied to the patient's veins, and damage the vein and surrounding tissue. In addition, some devices in the IV line are not made to withstand such a high pressure, and can leak when subjected to this pressure. It is, therefore, desirable and necessary to protect the patient/recipient from such dangerous, and possibly damaging, high pressure.

There are numerous examples of valves for use with IV (intravenous) administration sets and devices. However, valves, such as those shown and described in U.S. Pat. No. 4,146,055 patented on Mar. 27, 1979 to F. E. Ryder et al for "Valve Structure"; U.S. Pat. No. 4,230,300 patented on Oct. 28, 1980 to H. L. Wiltse for "Flow Metering and Shut-Off Valve"; and U.S. Pat. No. 4,332,369 patented on Jan. 1, 1982 to M. Gordon et al for "Adjustable In-Line Intravenous Valve With Locking Mechanism"; require human intervention to adjust the valves which are in no way automatically, and/or otherwise, self-responsive to changes in fluid-flow pressure. While a valve such as the one shown and described in U.S. Pat. No. 5,453,097 patented on Sep. 26, 1995 to J. R. Paradis for "Control of Fluid Flow" may very well permit fluid under unacceptable and dangerous pressures to flow into and out from the valve and from there to a person receiving the fluid infusion. There are also shown and described in U.S. Pat. No. 4,256,104 patented on Mar. 17, 1981 to A. J. Muetterties et al for "Equipment Sets and System For The Sequential Administration of Medical Liquids At Dual Flow Rates"; U.S. Pat. No. 4,316,460 patented on Feb. 23, 1982 to J. N. Genese et al for "Gravitational Flow System For The Sequential Administration of Medical Liquids"; and in U.S. Pat. No. 4,417,577 patented on Nov. 29, 1983 to J. N. Genese for "Gravitational Flow System For The Sequential Administration Of Medical Liquids"; but such systems are relatively complex and shut down one IV where a second one is turned on and then act to restrict air-flow when the second IV is finished.

Other valves intended for use with IV administration sets; such as, for example, those shown and described in U.S. Pat. No. 4,515,588 patented on May 7, 1985 to P. J. Amendolia for "I.V. Flow Regulator" and in U.S. Pat. No. 5,988,211 patented on Nov. 23, 1999 to W. D. Cornell for "I.V. Flow Controller" are provided for flow rate control, and in fact show, describe and teach that there are to be both inlet and outlet fluid-flow chambers and that the pressure in the outlet fluid-flow chamber has to exceed the pressure in the inlet fluid-flow chamber to permit passage of fluid to the patient and, as such, unacceptable high fluid-flow pressure entering the inlet chamber will necessitate an even higher and even more unacceptable fluid-flow pressure to the fluid recipient. On the other hand a pressure control valve, such as the one shown and described in U.S. Pat. No. 4,787,413 patented to J. M. Saggers on Nov. 29, 1988 for "Pressure Control Valve"; shows, describes and teaches the use of an intermittent on/off air-flow control that incorporates an inflatable sac that receives a bleed-off from an air duct to operate a plate that, in turn, moves a sealing device away from the opening of the air duct to permit air flow for the end use. The sac, however, when air flow pressure is reduced, returns air flow to the air duct and permits movement of the plate, under spring action, to move the sealing device back into position blocking the exit of air from the air duct and thus from the end use. The air entering the Saggers air-sac does not pass through the sac but is expelled, when expelled, through the air entry opening to the air sac. As such the valve is obviously only suitable for gasses and not for IV uses. It requires manual adjustment by a rotatable shaft and vents the air to the outside rather than confining it.

SUMMARY OF THE INVENTION

It is therefore an object of this invention to provide new and novel pressure responsive valves.

It is another object of this invention to provide new and novel fluid pressure responsive valves for incorporation into intravenous administration and infusion sets and systems.

It is yet another object of this invention to provide new and novel fluid pressure responsive valves for incorporation into intravenous administration sets and systems with relative ease, within the fluid-flow path between the source of the fluid and the patient/recipient that is to receive the fluid, and permits normal fluid flow with little or no flow restriction.

It is yet still another object of this invention to provide new and novel pressure responsive valves, primarily for IV use, which are relatively small in size and volume and which are bio-compatible.

It is yet still another object of this invention to provide new and novel pressure responsive valves, primarily for IV use, which respond to a predetermined "critical pressure".

It is yet still another object of this invention to provide new and novel pressure responsive valves, primarily for IV use, which work passively without operator adjustment and facilitate a normal fluid flow in safe fluid pressures independent of pressure applied to the fluid.

It is yet still another object of this invention to provide new and novel pressure responsive valves, primarily for IV use, which respond to pressures above a predetermined value to reduce or cut-off inflow of fluid to a pressure sensing device while maintaining uninterrupted flow to the recipient.

It is yet still another object of this invention to provide new and novel pressure responsive valves, primarily for IV use, for incorporation into or with a fluid warmer.

It is still another object of this invention to provide new and novel fluid pressure responsive valves, primarily for IV use, that are constructed of materials so that the fluid-flow path can be sterilized and made non-pyrogenic by conventional methods and so that single use thereof is economically feasible.

Other objects of this invention will hereinafter become obvious from the following description of the preferred embodiments of this invention.

The instant pressure response valve (PRV) incorporates a deformable sensor chamber. The geometry of the sensor chamber allows normal fluid-flow to proceed with very low flow restriction when the applied pressure is well below a predetermined "critical value". When the fluid pressure is at or exceeds the "critical value" the valve functions by change of the geometric configuration of the sensing chamber with sufficient force to either overcome the input pressure seen in the chamber or by action of a valve member to crimp fluid flow tubing to the sensing chamber; or by deforming so as to activate a feature in the valve to cut off fluid flow into the sensor chamber; all without interfering with outflow from the valve to the intended use or user. The pressure in the valve is automatically reduced below the "critical value" by the continued fluid flow from the sensing chamber, or part of the chamber, to once again permit fluid inflow. The pressure responsive valve (PRV) utilizes a small number of simple plastic components to accomplish the pressure limiting function, and to maintain very small size, and small priming volume. The components contacting the fluid are relatively easily formed by injection molding or by welding or sealing tubing components, and are presumably sterilizable by conventional means. Example embodiments of simplified valves employing these mechanisms are shown in the detailed description that follows:

DESCRIPTION OF THE INVENTIVE EMBODIMENTS

Figure 1:
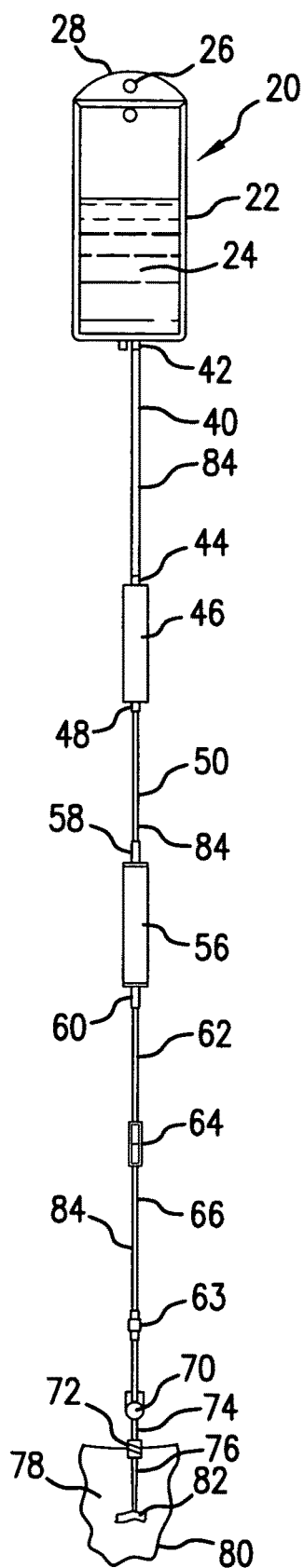
FIG. 1 is a partially schematic view of an IV administration set or system incorporating and embodying the principles of and the instant invention.
Figure 4:
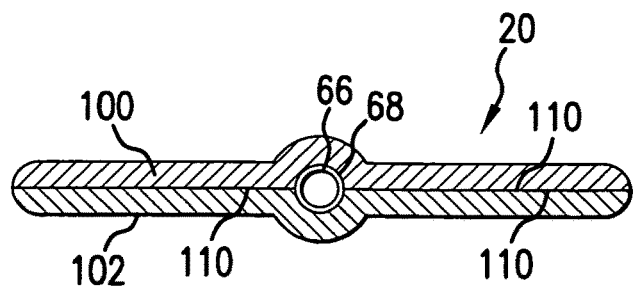
FIG. 4 is a schematic section taken on line 4-4 of FIG. 2.

With reference to FIG. 1 there is generally shown at 20 an intravenous IV administration set or system including a reservoir 22, which, by way of example, may be a pouch or fluid bag containing any of a multiple of different fluids or infusate 24 appropriate for infusion into a recipient (which could be a person, animal or the like) as will be hereinafter explained. An opening 26 facilitates providing a handle 28 for reservoir 22 to facilitate carrying and/or hanging of same for use. A tube 40, of conventional construction, connects an output port 42 of reservoir 22 to an inlet port 44 of a conventional drip chamber 46; the outlet port 48 of which is connected to a tube 50. A hand pump, bladder, or squeeze pump 56 may be incorporated into IV set 20, to facilitate increasing pressure on the flow of fluid infusate 24 should that be necessary, by having its input port 58 connected to tube 50 and its output port 60 connected to a tube 62. Tube 62 also connects to a conventional fluid-flow control valve or roller clamp 64 which is, in turn, connected by a tube 66 to an input port 68 of a pressure responsive fluid-flow valve 70 incorporating the instant invention. An output port 72 of pressure responsive valve 70 is connected by a tube 74 to a needle or cannula 76 that is usually inserted into an arm 78 of a patient 80 for delivery of the potential infusate 24 flowing from reservoir 22.

Tubes 40, 50, 62, 66 and 74 are of conventional construction and use; as are drip chamber 46, bladder 56, and hypodermic needle 76 to a patient/recipient 80. A piece of tape 82 may be utilized to secure needle 76 in place. Thus it should be clear that tubes 40, 50, 62 and 66 and drip chamber 44, bladder 56, valve 64, pressure responsive valve 70, tube 74 and needle 76 together define a fluid-flow path 84 for the delivery of IV fluid 24 from reservoir 22 to a patient/recipient 78. It should be understood that while the various components of IV set 20 have been shown as connected and described herein that other suitable connections may be utilized and additional and/or other components may be employed for IV set or system 20.

Figure 5:
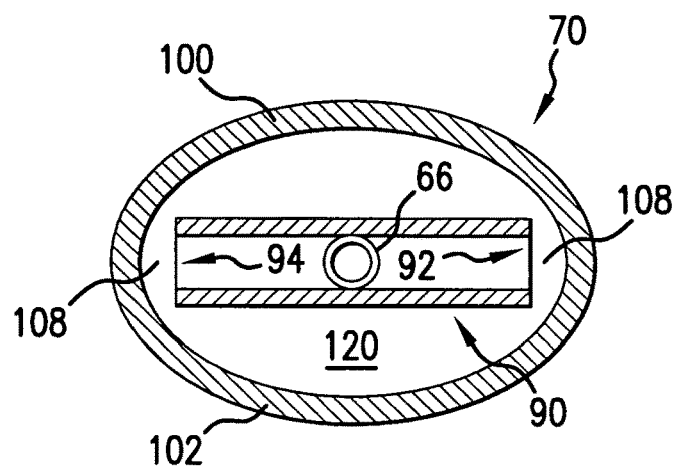
FIG. 5 is a schematic section taken on line 5-5 of FIG. 2 and showing the pressure responsive valve as it would be ready to receive fluid and/or as it would receive fluid with a pressure less then a "critical pressure" for the pressure responsive valve.
Figure 6:
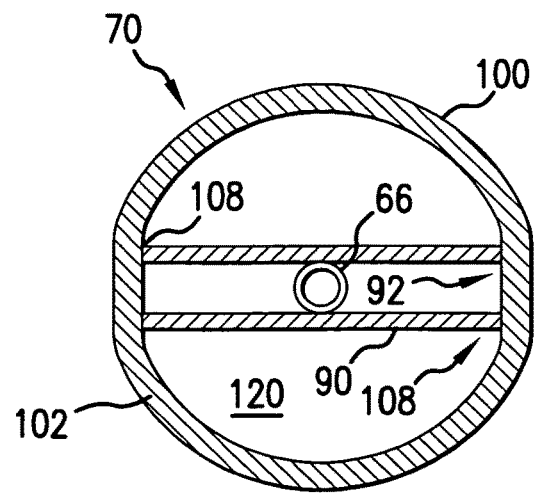
FIG. 6 is a schematic section also taken on line 5-5 of FIG. 2 showing the pressure responsive valve as it would be responding to fluid at or above the critical pressure.
Figure 2:
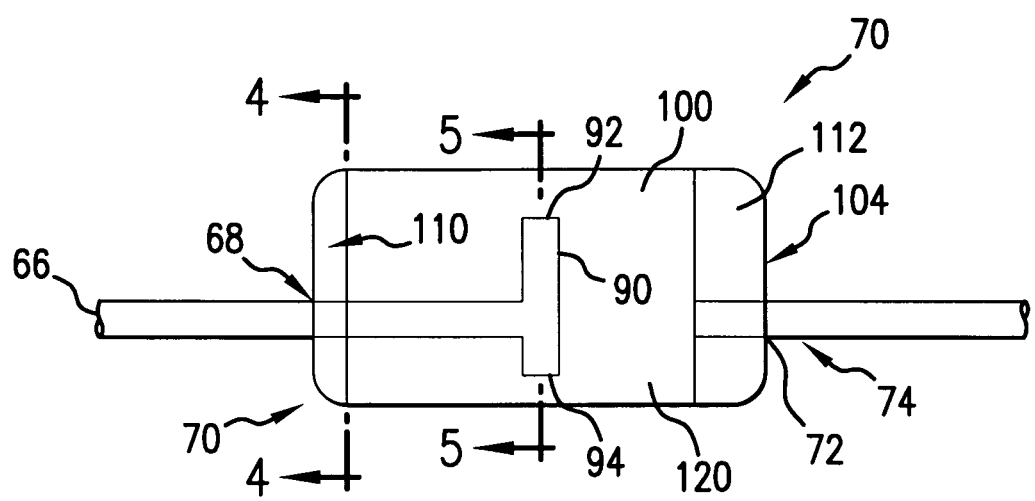
FIG. 2 is a schematic plan view of a pressure responsive valve incorporating the instant invention.
Figure 3:
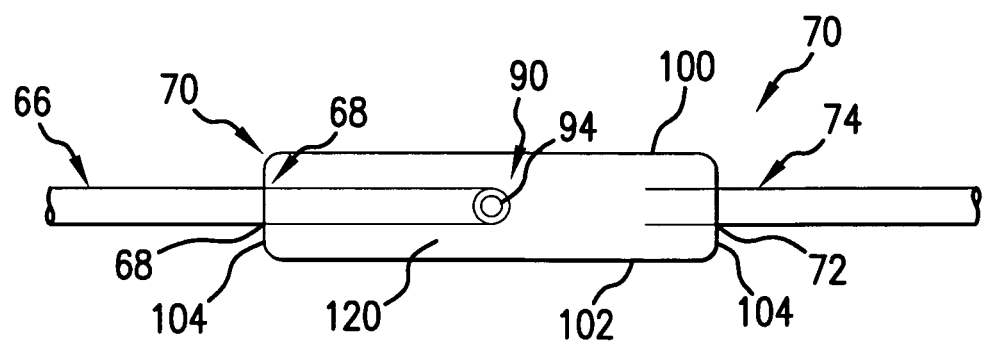
FIG. 3 is a schematic side view of the pressure responsive valve of FIG. 2.

Tube 66 (FIGS. 1-4) extends through input port 68 of pressure responsive valve 70 and terminates at a "T" tube 90 (FIGS. 1-3, 5 & 6) open at its ends 92 and 94. Pressure responsive valve 70 is fabricated in general as a tube from the same materials as tubes 40, 50, etc. but so as to have a somewhat larger diameter and, for purposes of this specification may be considered to have an upper wall 100 (FIGS. 2-6) and a lower wall 102 (FIGS. 3-6). A portion of the tube stock from which valve 70 is to be fabricated is cut to a selected length and welds 110 (FIGS. 2 & 4) and 112 (FIG. 2) are fabricated at respective ends thereof to secure upper wall 100 and lower wall 102 together to form valve 70 into a pillow like configuration. Weld 110 also secures tube 66 in place so that "T" tube 90 is properly positioned in pressure responsive valve 70 at a pressure responsive zone 108 as shown in FIGS. 5 & 6; while weld 112 also secures tube 74 (FIG. 1) in place at output port 72 of pressure responsive valve 70. Upper wall 100, lower wall 102 are fabricated from plastic materials which are transparent or translucent and which posses a predetermined amount of resilience and flexibility. The sizing and configuration of walls 100 and 102 is selected so that when tubes 66 and 72 are in place and with "T" tube 90 extending as shown from input tube 66 welds 110, 112 are applied so that valve 70 assumes said "pillow-like" configuration enclosing a sensing space or chamber 120 within inner surfaces of walls 100 and 102 and welds 110, 112. It should be noted that the normal, usual or at-rest configuration for valve 70 is an oval (FIG. 5).

When pressure responsive valve 70 is installed in IV set 20 (FIG. 1) fluid infusate 24 from reservoir 22 will follow fluid-flow path 84 entering pressure responsive valve 70 through tube 66, and input port 68 and "T" tube 90, exiting valve 70 through exit port 72 and tube 74, to its end use such as by a patient/recipient 78. As long as the pressure exerted by fluid 24 is below a predetermined "critical pressure" valve 70 will remain in its oval configuration, with its walls 100 and 102 spaced from open ends 92, 94 of "T" tube 90. As such fluid 24 will flow from ends 92, 94 of "T" tube 90 into sensing space 120 and therefrom out of valve 70 through its exit port 72 and tube 74. Should the pressure within valve 70 rise above the predetermined "critical pressure" fluid 24 within sensing space 120 will induce walls 100, 102 and 104 of valve 70 to assume a circular or near circular configuration as shown in FIG. 6. Walls 100 and 102 will approach or even touch ends 92, 94 of "T" tube 90 and the flow of fluid 24 from those ends will either stop or be curtailed. However, the fluid 24 already in sensing chamber 120, will continue to flow through exit port 72 and thereafter along flow path 84 to a recipient/patient 78 because of the fluid pressure in the sensing chamber.

As fluid 24 exits sensing space 120 the fluid pressure therein will automatically and with no operator intervention be reduced below the "critical limit". Walls 100, 102 and 104, due to the material and fabrication thereof, will return to their oval disposition (FIG. 5) where they are spaced from ends 92, 94, of "T" tube 90. However, the fluid 24 already in sensing chamber 120 will be at elevated pressure (near the critical pressure) and fluid will continue to flow out of valve 70 through exit port 72 and therefore along fluid path 84 to a recipient/patient 78.

Figure 7:
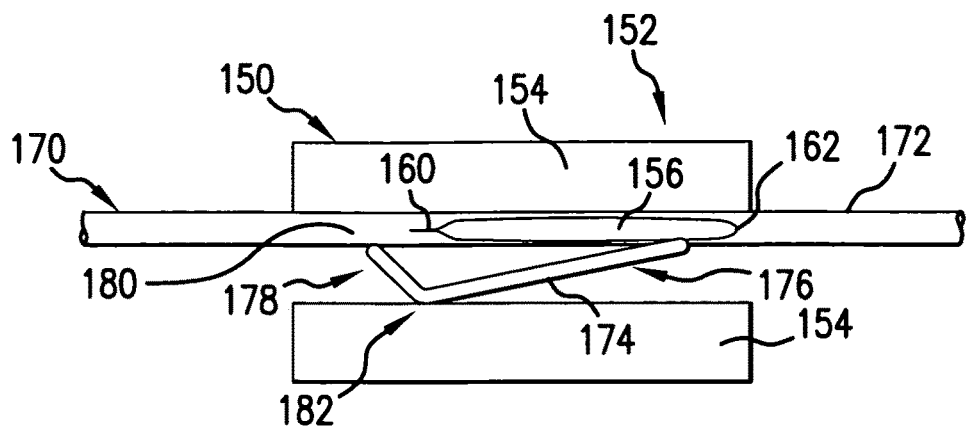
FIG. 7 is a schematic side view of still another alternative embodiment of pressure responsive valve incorporating the instant invention.

With reference to FIG. 7 there is shown an alternative embodiment of pressure responsive valve 150 that could be incorporated into an IV administration set or system 152, similar to IV set 20 (FIG. 1), and at a location in IV set 152 similar to that of pressure responsive valve 70 of IV set 20. Valve 150 is disposed in a housing 154 sized and configured to receive a sensing tube or chamber 156, which is fabricated from materials similar to that of sensing chamber 120 of IV set 20 of FIG. 1 and with welds 160, 162 proximate the ends of tube 156 so that tube 156 is disposed in an oval, pillow-like, configuration. Weld 160 also serves to retain inflow tube or entry 170 in place as an entry into sensing tube or chamber 156; while weld 162 serves to retain outflow or exit tube 172 in place as an exit or outflow from sensing tube 156. An action lever 174 is positioned in housing 154 so that its response arm 176 is disposed in contact with sensing chamber 156 and so that its pinch arm 178 is disposed in contact with or proximate to a pinch or restriction zone 180 for inflow tube 170 proximate where it enters sensing chamber 156 but outside sensing chamber 156. A pivot 182 is formed where pinch arm 178 meets response arm 176. The angle at which pinch arm 178 meets response arm 176, and the relative lengths and widths of same are selected to provide appropriate coaction between action lever 174 and sensing tube/pillow 156 and commensurate operation of valve 150.

Tube 170 and valve 150 are incorporated into IV set 152 at a suitable location so that the outflow from the IV reservoir (not shown) and IV set components that receive that outflow becomes the fluid inflow through tube 170 and into sensing chamber 156. As long as the pressure exerted on, or by, such fluid remains under a selected "critical pressure limit" the flow of the IV fluid will continue through valve 150 and outflow tube 172 and thence to the recipient of the IV infusion. Should the pressure on and exerted by the IV fluid reach the "critical limit" or be in excess thereof, the oval/pillow like configuration of sensing chamber 156 will become rounder (less oval) and that occurrence will effect a reaction of sensing chamber 156 with response arm 176 of action lever 174 to pivot action lever 174 clockwise (FIG. 7) about pivot 182 and move pinch arm 178 against inflow tube 170 at pinch/restriction zone 180 to thus reduce or cut-off inflow of the fluid into sensing chamber 156. The flow of the fluid that is already in sensing chamber 156, however, will continue, under pressure, to flow from sensing chamber 156 and out through exit/outflow port 172. As such the fluid pressure within and exerted by sensing chamber 156 on response arm 176 of action lever 174 will diminish permitting the inflow of fluid through inflow tube 170 to urge pinch arm 178 to pivot counterclockwise about pivot 182 and response arm 176 to follow sensing chamber 156 as it returns from its reactive circular configuration to its normal oval configuration.

Figure 8:
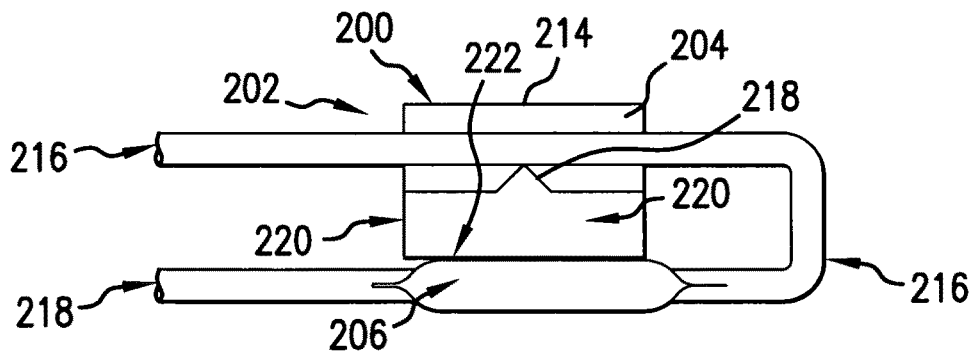
FIG. 8 is a schematic side view of yet another alternative embodiment of pressure responsive valve incorporating the instant invention.

FIG. 8 shows another alternative embodiment of pressure responsive valve 200 that could be incorporated into an IV administration set or system 202, similar to IV set 20 (FIG. 1), and at a location in IV set 202 similar to that of pressure responsive valve 70 of IV set 20. Valve 200 is disposed in a housing 204 sized and configured to receive a sensing tube or chamber 206, which is fabricated from materials similar to that of sensing chamber 120 (FIG. 1) of IV set 20 and sensing chamber 156 (FIG. 7) of IV set 152 and with welds 210 and 212 proximate the ends of chamber 206 so that sensing chamber 206 is disposed in an oval/pillow-like configuration. Weld 210 also serves to retain inflow tube or entry 216 in place as an entry into sensing chamber 206; while weld 218 serves to retain outflow or exit tube 218 in place as an exit or outflow from sensing chamber 206. A movable piston 220 is positioned in housing 204 in contact with an action wall 222 of sensing chamber 206 and for movement towards and away from a pinch/restriction zone 224 of inflow tube 216. A pinch valve 218 is carried by piston 220 for coaction with fluid inflow tube 216 at pinch/restriction zone 224.

Inflow tube 216 and pillow-like sensing chamber 206 are incorporated into IV set 202 at a suitable location so that outflow from the IV reservoir (not shown) and IV set components that receive fluid therefrom (not shown) becomes the fluid inflow through tube 216 and into sensing chamber 206. As long as the pressure exerted on or by such fluid remains under a selected "critical pressure" or "critical limit" the flow of the IV fluid will continue through valve 200 and outflow tube 218 and thence to the recipient of the IV infusion. Should the pressure on and exerted by the IV fluid reach the "critical pressure limit" or be in excess thereof, the oval/pillow-like configuration of sensing chamber 206 becomes rounder (less oval) and that occurrence will effect a reaction of action wall 222 of sensing chamber 206 with piston 220 to move pinch valve 228 against and into inflow tube 216 at pinch/restriction zone 224 to thus reduce or cut-off inflow of the IV fluid into sensing chamber 206. The flow of the IV fluid that is already in sensing chamber 206, however, will continue, under pressure, to flow from sensing chamber 206 and out through exit/outflow port 218. As such the fluid pressure within and exerted by sensing chamber 206 will automatically diminish allowing sensing chamber 206 to return to its oval/pillow-like configuration and its action wall 222 on piston 220 will diminish permitting the inflow of IV fluid through inflow tube 216 through sensing chamber 206 and therefrom to the recipient of the infusion.

Figure 9:
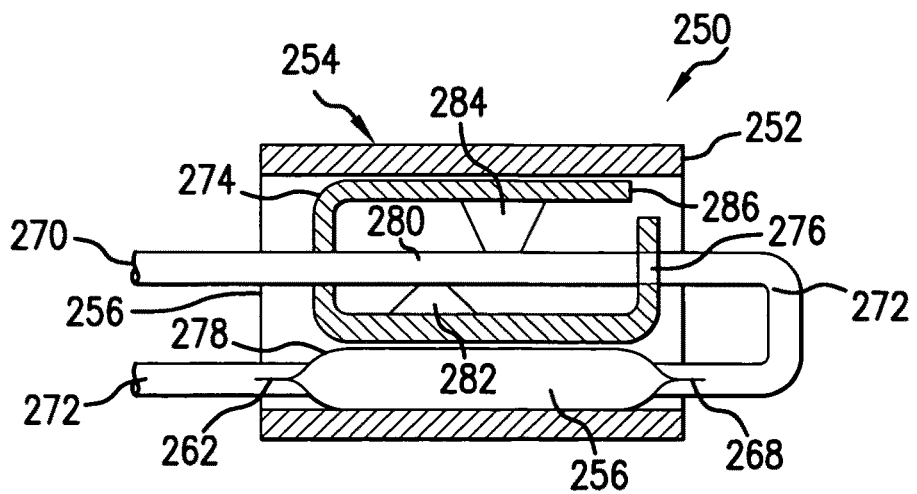
FIG. 9 is a schematic side view of yet still another alternative embodiment of pressure responsive valve incorporating the instant invention.

FIG. 9 shows another alternative embodiment of pressure responsive valve 250 that could be incorporated into an IV administration set or system 252, similar to IV set 20 (FIG. 1), and at a location in IV set 252 similar to that of pressure responsive valve 70 of IV set 20. Valve 250 is disposed in a housing 254 sized and configured to receive a sensing tube or chamber 266, which is fabricated from materials similar to that of sensing chamber 120 (FIG. 1) of IV set 20 and sensing chamber 156 (FIG. 7) of IV set 152 and with welds 260 and 262 proximate the ends of chamber 256 so that sensing chamber 256 is disposed in an oval/pillow-like configuration. Weld 260 also serves to retain inflow tube or entry 270 in place as an entry into sensing chamber 256; while weld 262 serves to retain outflow or exit tube 272 in place as an exit or outflow from sensing chamber 256. A reaction device 274 is positioned in housing 254 so that a relatively flexible action arm 276 thereof is in contact with an action wall 278 of sensing chamber 256 and for movement towards and away from a pinch/restriction zone 280 of inflow tube 270. A pinch valve 282 is carried by arm 276 for coaction with fluid inflow tube 270 at pinch/restriction zone 280. A pinch piece 284 extends from another arm 286 of reaction device 274 towards and for coaction with pinch valve 282 at pinch/restriction zone 280.

Inflow tube 270 and pillow-like sensing chamber 256 are incorporated into IV set 252 at a suitable location so that outflow from the IV reservoir (not shown) and IV set components that receive fluid therefrom (not shown) becomes the fluid inflow through tube 270 and into sensing chamber 256. As long as the pressure exerted on or by such fluid remains under a selected "critical pressure or limit" the flow of the IV fluid will continue through valve 250 and outflow tube 272 and thence to the recipient of the IV infusion. Should the pressure on and exerted by the IV fluid reach the "critical pressure limit" or be in excess thereof, the oval/pillow-like configuration of sensing chamber 256 becomes rounder (less oval) and that occurrence will effect a reaction of action wall 278 of sensing chamber 256 with action arm 276 to move pinch valve 282 against and into inflow tube 270 at pinch/restriction zone 280, and in coaction with pinch piece 284 to reduce or cut-off inflow of the IV fluid into sensing chamber 256. The flow of the IV fluid that is already in sensing chamber 256, however, will continue, under pressure, to flow from sensing chamber 256 and out through exit/outflow port 272. As such the fluid pressure within and exerted by sensing chamber 256 will reduce allowing sensing chamber 256 to return to its oval/pillow-like configuration and its action wall 276 on piston 274 will diminish permitting the inflow of IV fluid through inflow tube 272 through sensing chamber 256 and therefrom to the recipient of the infusion.

Another embodiment of pressure responsive valve 300 (FIG. 10) includes a housing or main body 302 within which there is disposed a valve operator 308. Housing 302 and valve operator 308 may be fabricated from materials similar to those described above for the other embodiments and may be circular, square, rectangular or of any other suitable horizontal or vertical cross-section configuration. Valve operator 308 includes a flexible silicone diaphragm 310 with a stem 312 extending from its bottom wall and with stem 312 terminating at a piston-like valve cap 316. Diaphragm 310 is seated on a rim 318 that surrounds an inner wall 320 of housing 302. A valve seat 330, that surrounds valve stem 312, is supported by a first ledge 332, that extends out from wall 320 of housing 302 and a second ledge 334 that is supported by a leg 336 that extends out from a wall 338 of housing 302. First ledge 332 and second ledge 334 surround but are spaced from valve stem 312 to form a fluid passageway 340 between a fluid entry or in-flow chamber 342 for valve 302 and a fluid outflow or exit chamber 344 for valve 302. A fluid inflow tube 346 is utilized to connect pressure responsive valve 302 into an IV set or system, of the type described hereinabove and shown in FIG. 1, through an input port 348 of input chamber 342; while a fluid outflow tube 350 is utilized to connect pressure responsive valve 302 into an IV set or system through an output port 352 of output chamber 344 of valve 302. A cap 354, providing a cover for valve 300, includes a vent hole 356.

IV fluid entering inflow chamber 342, of pressure responsive valve 300, through tube 346, flows through fluid passage 340 and into outflow or exit chamber 344 and then through outflow tube 350 to either other components of the IV set or system or to the intended recipient of the fluid. Should the pressure of, or exerted by, the fluid exceed a "critical limit pressure" the fluid in outflow chamber 344 will exert sufficient pressure on an underside of diaphragm 310 and move valve operator 308 along inner wall 320 of housing 302 until valve cap 316 seats against valve seat 330 and closes fluid passage 340 and the flow of fluid from input chamber 312 into output chamber 344. Since there are no obstructions to fluid flow out from chamber 344 the fluid will flow from chamber 344 through tube 350 and then to other components of the IV set or system and/or then to the recipient of the fluid. As the fluid continues to so flow the pressure in chamber 344 will diminish without operator intervention and diaphragm 310 will move along wall 320 of housing 302 until valve cap 316 moves away from valve seat 330 to again permit fluid flow into valve 300 and on to the recipient all automatically and without operator involvement.

Figure 10:
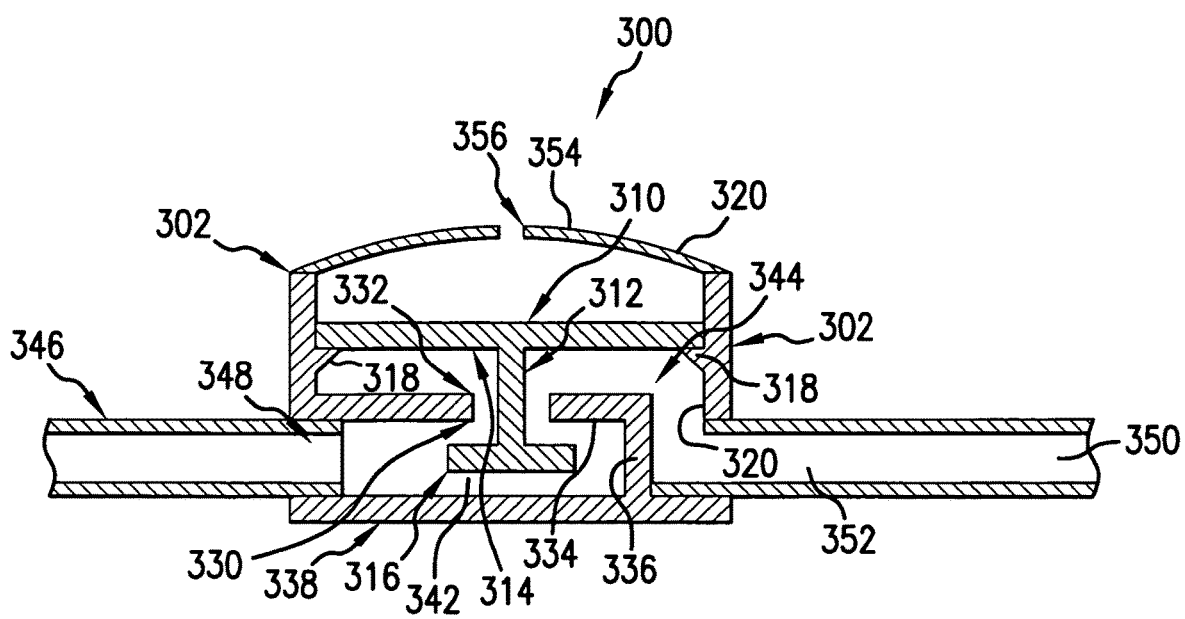
FIG. 10 is a schematic side view of yet still another alternative embodiment of pressure responsive valve incorporating the instant invention.

Another embodiment of pressure responsive valve 400 (FIG. 11), similar to but different from the embodiment of FIG. 10, includes a housing or main body 402 within which there is disposed a piston-like valve operator or action device or means 408. Housing 402 and valve action device or means operator 408 may be fabricated from materials similar to those described above for the other embodiments and may be circular, square, rectangular or of any other suitable horizontal or vertical cross-section configuration. Valve operator 408 includes an elastic flexible silicone diaphragm 410 with a stem 412 extending from its bottom wall and with a piston-like stem 412 terminating at a piston-like valve cap 416.

Figure 11:
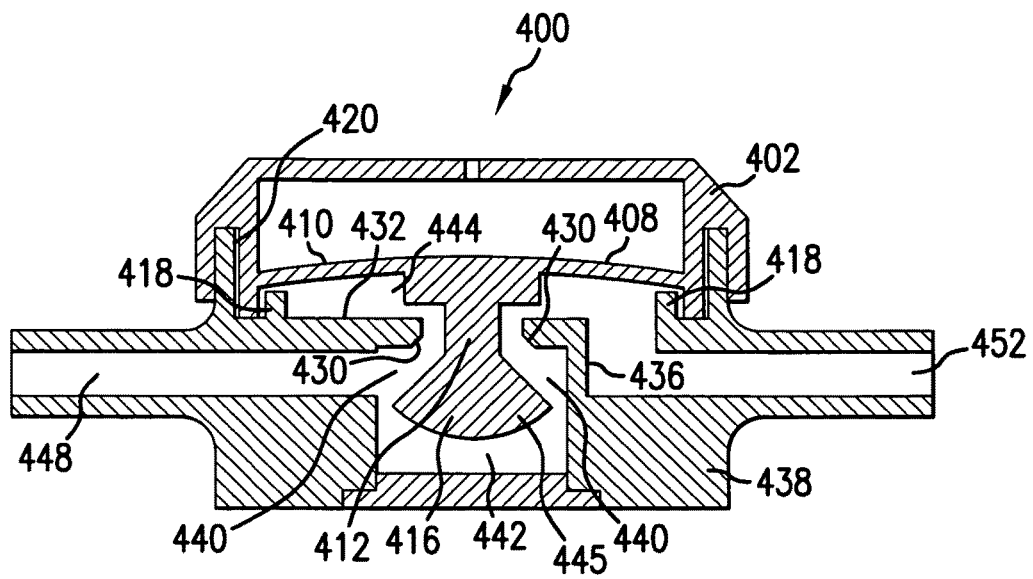
FIG. 11 is a schematic side view of yet still another alternative embodiment of pressure responsive valve incorporating the instant invention.

Diaphragm 410 is seated on a rim 418 that surrounds an inner wall 420 of housing 402, and when seated thereon, as can be readily seen from FIG. 11, is disposed bulging upwardly in a convex configuration or disposition thereupon. A tapered valve or piston seat 430, that surrounds valve stem 412, is formed at a lower end of a first ledge 432, that extends out from wall 420 of housing 402 and a second ledge that is supported by a leg 436 that extends out from a wall 438 of housing 402. Valve or piston seat 430 surrounds but is spaced from valve stem 412 to form a fluid passageway 440 between a fluid entry or in-flow of a first sensing, chamber 442 for valve 400 and a fluid outflow or exit of a second sensing chamber 444 for valve 400. Sides 445 of valve stem 412 are tapered down and out for co-action with correspondingly tapered valve seat 430. Valve action device or operator 408 and valve seat 430 together form a fluid pressure sensor or, sensing arrangement A fluid inflow tube, of the type described for previously described embodiments, is utilized to connect pressure responsive valve 400 into an IV set or system, of the type described hereinabove and shown in FIG. 1, through an input port 448 of a fluid entry or input chamber 442; while a fluid outflow tube of similar size and construction is utilized to connect pressure responsive valve 400 into an IV set or system through an output port 452 of a fluid exit or output chamber 444 of valve 400.

Diaphragm 410 is seated on a rim 418 that surrounds an inner wall means 420 of housing 402, and when seated thereon, as can be readily seen from FIG. 11, is disposed bulging upwardly [in a convex configuration or disposition thereupon]. As such, and, also as can be readily seen in FIG. 11, diaphragm 410 when so disposed provides an upper surface curved downwardly in a convex configuration and an under or lower surface curved in a concave configuration. A tapered valve seat 430, that surrounds valve stem 412, is formed at a lower end of a first ledge 432, that extends out from wall 420 of housing 402 and a second ledge that is supported by a leg 436 that extends out from a wall 438 of housing 402. Valve seat 430 surrounds but is spaced from valve stem 412 to form a fluid passageway 440 between a fluid entry or in-flow chamber 442 for valve 400 and a fluid outflow or exit chamber 444 for valve 400. Sides 445 of valve stem 412 are tapered down and out for co-action with correspondingly tapered valve seat 430. Valve action device or operator 408 and valve seat 430 together form a fluid pressure sensing arrangement A fluid inflow tube of the type described for previously described embodiments, is utilized to connect pressure responsive valve 400 into an IV set or system, of the type described hereinabove and shown in FIG. 1, through an input port 448 of a fluid entry or input chamber 442; while a fluid outflow tube of similar size and construction is utilized to connect pressure responsive valve 400 into an IV set or system through an output port 452 of a fluid exit or output chamber 444 of valve 400.

IV fluid entering the first or inflow chamber 442, of pressure responsive valve 400, through input port 448, flows through fluid passage 440 and into a second or outflow or exit chamber 444 and then through output port tube 452 to either other components of the IV set or system or to the intended recipient of the fluid. The inherent elasticity of flexible diaphragm 410 when reacting to fluid pressure in exit chamber 444 stretches diaphragm 410 upwardly, placing diaphragm 410 in tension, while that inherent tension and elasticity permit diaphragm 410 to return towards its FIG. 11 disposition or configuration; assuming various concave dispositions or configurations there between. Should the pressure of, or exerted by, the fluid exceed a "critical limit pressure" the fluid in outflow chamber 444 will exert sufficient pressure on an underside of diaphragm 410 to flex diaphragm 410 and move valve cap 416 to seat same against valve seat 430 and close fluid passage 440 and the flow of fluid from input chamber 442 into output chamber 444. Since there are no obstructions to fluid flow out from chamber 444 the fluid will flow from chamber 444 through port 450 and then to other components of the IV set or system and/or then to the recipient of the fluid. As the fluid continues to so flow the pressure in chamber 444 will diminish without operator intervention and diaphragm 410 will flex or return back until valve cap 416 moves away from valve seat 430 to again permit fluid flow into valve 400 and on to the recipient all automatically and without operator involvement.

The instant pressure responsive valves (PRV's) operate as a simple components of IV infusion sets and/or systems. The set must be a closed system to maintain both sterility of the infusate, and not expose workers in the field to unsafe fluids. The PRV's are constructed of materials so that the fluid path is biocompatible-compatible with blood products, and does not leach out any substance which is harmful to tissue. Its flow path is readily sterilized and rendered pyrogen free by commonly used means. It is relatively small, with small priming volume, and capable of being placed in-line in the set. It does not contain any electrical components. It operates passively, without requiring the user to make any adjustments or settings and can deliver infusate at unregulated pressures 0 to greater than 1500 mm Hg.

The instant pressure responsive valves allow for sudden increase in flow so long as the applied pressure remains below a "critical pressure limit or value", (in the range of about 250 to 350 mm Hg for instance). The valve has a minimal flow resistance when used at typical IV pressures of 50-100 mm Hg, as well as at increased pressures which are below the said "critical value". The respective valves are formed to provide valves of single "critical pressure limits or values". It being understood that valves with other "critical pressure limits or values" may be fabricated depending on proposed uses and fluids to be infused.

The present invention can be used as a separate device in an IV set, can be built into a fluid administration set, or can be integrated into an existing device. The described PRV embodiments may, for example, be permanently bonded to the inflow tubing of a device such as the Blood Heater Disposable Set, which is one embodiment of U.S. Pat. No. 6,480,257, "Heat Exchanger Usable in Wearable Fluid Heater." to protect the device from excessive pressure, or to protect the patient distal to the device, from excessive pressure. The disclosed PRV's may be fabricated with luer or other fittings for insertion into an IV administration set or system.

While only certain specific preferred embodiments of the invention have been described, it is understood that many variations thereof are possible without departing from the principals of this invention as defined in the following claims.

A fluid pressure sensing device is formed with a fluid entry chamber and a fluid exit chamber interconnected by a passageway and provided with a piston that reacts to an increase in fluid pressure above a predetermined amount to close off the interconnection between the chambers and fluid flow into the exit chamber. The piston depends from an elastic flexible diaphragm that is disposed in a first convex configuration such that pressure in the fluid exit chamber coacts with the diaphragm to bulge and stretch same under tension and, should that pressure reach or exceed a predetermine "critical pressure" the stretching diaphragm will move into a second disposition closing the passageway between the fluid entry and exit chambers. Continued fluid flow from the exit chamber results in a reduction of fluid therein and permits the inherent tension of the diaphragm to move the diaphragm from its second disposition thus reopening of the fluid passageway between the chambers.

What is claimed is:

1. A fluid pressure responsive valve for use in delivery of an IV infusate to a patient, the valve comprising:
an input port;
an inflow chamber;

a pressure sensor;
an outflow chamber; and
an output port,
wherein the input port receives the IV infusate and directs the IV infusate to the inflow chamber,
wherein a wall of the inflow chamber comprises a valve seat,
wherein the pressure sensor reacts to changes of fluid pressure in the outflow chamber, and comprises a valve operator and a valve cap,
wherein the valve operator comprises a concave wall from the perspective of the outflow chamber,
wherein the fluid pressure responsive valve does not comprise a spring, and wherein the valve operator is connected to the valve cap such that when fluid pressure in the outflow chamber is in excess of a critical limit, the concave wall stretches, thereby displacing the valve cap to seat against the valve seat so that fluid from the inflow chamber to the outflow chamber is restricted and/or closed-off without a spring, whereby flow of the IV infusate from the inflow chamber to the outflow chamber is only permitted when the fluid pressure in the outflow chamber is less than the critical limit,
wherein the valve seat is tapered,
wherein a side of the valve cap is tapered,
wherein the output port directs the IV infusate from the outflow chamber to the patient,
wherein the input port and the output port are parallel,
wherein the fluid pressure responsive valve is sterilizable, and non-pyrogenic, and
wherein the critical limit is in a range from 250 to 350 mm Hg.

2. The fluid pressure responsive valve of claim 1, wherein the fluid pressure responsive valve is biocompatible.

3. The fluid pressure responsive valve of claim 2, wherein the fluid pressure responsive valve is compatible with blood products.

4. The fluid pressure responsive valve of claim 2, wherein the fluid pressure responsive valve does not leach out any substance which is harmful to tissue.

5. The fluid pressure responsive valve of claim 1, wherein the concave wall comprising an elastic flexible diaphragm.

6. The fluid pressure responsive valve of claim 5, wherein the elastic flexible diaphragm comprises silicone.

* * * * *

UNITED STATES PATENT AND TRADEMARK OFFICE
CERTIFICATE OF CORRECTION

PATENT NO. : 11,123,484 B2
APPLICATION NO. : 12/228618
DATED : September 21, 2021
INVENTOR(S) : John Joseph Landy, III et al.

Page 1 of 1

It is certified that error appears in the above-identified patent and that said Letters Patent is hereby corrected as shown below:

On the Title Page

In the Abstract:
Line number 20, please replace "eit chamber" with "exit chamber".

In the Claims

At Column 12, Claim number 5, Line number 19, please replace "comprising" with "comprises".

Signed and Sealed this
Twenty-third Day of November, 2021

Drew Hirshfeld
*Performing the Functions and Duties of the*
*Under Secretary of Commerce for Intellectual Property and*
*Director of the United States Patent and Trademark Office*